United States Patent
LaBaer et al.

(10) Patent No.: US 12,085,569 B2
(45) Date of Patent: *Sep. 10, 2024

(54) PLASMA AUTOANTIBODY BIOMARKERS FOR BASAL LIKE BREAST CANCER

(71) Applicants: ARIZONA BOARD OF REGENTS ON BEHALF OF ARIZONA STATE UNIVERSITY, Scottsdale, AZ (US); THE UNITED STATES OF AMERICA, AS REPRESENTED BY THE SECRETARY, DEPARTMENT OF HEALTH AND HUMAN SERVICES, Bethesda, MD (US)

(72) Inventors: Joshua LaBaer, Chandler, AZ (US); Jie Wang, Glendale, AZ (US); Ji Qiu, Chandler, AZ (US); Garrick Wallstrom, Mesa, AZ (US); Karen Anderson, Scottsdale, AZ (US); Jin Park, Phoenix, AZ (US); Jonine Figueroa, Edinburgh (GB)

(73) Assignees: ARIZONA BOARD OF REGENTS ON BEHALF OF ARIZONA STATE UNIVERSITY, Scottsdale, AZ (US); THE UNITED STATES OF AMERICA, AS REPRESENTED BY THE SECRETARY, DEPARTMENT OF HEALTH AND HUMAN SERVICES, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/940,883

(22) Filed: Sep. 8, 2022

(65) Prior Publication Data

US 2023/0079737 A1     Mar. 16, 2023

Related U.S. Application Data

(63) Continuation of application No. 16/743,906, filed on Jan. 15, 2020, now Pat. No. 11,525,831, which is a continuation of application No. 15/534,203, filed as application No. PCT/US2015/064792 on Dec. 9, 2015, now abandoned.

(60) Provisional application No. 62/089,631, filed on Dec. 9, 2014.

(51) Int. Cl.
G01N 33/574    (2006.01)
C07K 16/30     (2006.01)
C12Q 1/6886    (2018.01)
G01N 33/564    (2006.01)
C12N 15/11     (2006.01)

(52) U.S. Cl.
CPC ... G01N 33/57415 (2013.01); C07K 16/3015 (2013.01); C12Q 1/6886 (2013.01); G01N 33/564 (2013.01); C12N 15/11 (2013.01); C12Q 2600/112 (2013.01); C12Q 2600/118 (2013.01); C12Q 2600/158 (2013.01)

(58) Field of Classification Search
CPC .................................................. G01N 33/57415
USPC ............................................................. 435/6.14
See application file for complete search history.

(56) References Cited

U.S. PATENT DOCUMENTS

| | | |
|---|---|---|
| 9,442,111 B2 | 9/2016 | Lindsay |
| 9,535,070 B2 | 1/2017 | Saul |
| 9,857,374 B2 | 1/2018 | Labaer |
| 9,938,523 B2 | 4/2018 | Labaer |
| 10,045,990 B2 | 8/2018 | Festa |
| 10,435,747 B2 | 10/2019 | LaBaer |
| 10,648,978 B2 | 5/2020 | Wang |
| 10,717,977 B2 | 7/2020 | LaBaer |
| 10,787,710 B2 | 9/2020 | LaBaer |
| 10,802,026 B2 | 10/2020 | LaBaer |
| 11,525,831 B2 * | 12/2022 | LaBaer ............... G01N 33/564 |
| 2009/0239229 A1 | 9/2009 | Weaver |
| 2010/0204055 A1 | 8/2010 | Bonner-Ferraby et al. |
| 2011/0150935 A1 | 6/2011 | Grigoriadis |
| 2014/0162902 A1 | 6/2014 | Labaer |
| 2014/0371091 A1 | 12/2014 | Wiktor |
| 2015/0362497 A1 | 12/2015 | Anderson |
| 2016/0041159 A1 | 2/2016 | Labaer |
| 2016/0195546 A1 | 7/2016 | Labaer |
| 2017/0045515 A1 | 2/2017 | Anderson |
| 2017/0115299 A1 | 4/2017 | Saul |
| 2017/0176423 A1 | 6/2017 | Anderson |
| 2017/0356029 A1 | 12/2017 | Krajmalnik-Brown |
| 2018/0320230 A1 | 11/2018 | Labaer |

(Continued)

FOREIGN PATENT DOCUMENTS

| | | |
|---|---|---|
| WO | 2012021887 A2 | 2/2012 |
| WO | 2013019680 A1 | 2/2013 |

(Continued)

OTHER PUBLICATIONS

Anderson, Karen S., et al. "Protein microarray signature of autoantibody biomarkers for the early detection of breast cancer." Journal of proteome research 10.1 (2011): 85-96.

(Continued)

*Primary Examiner* — Sean E Aeder
(74) *Attorney, Agent, or Firm* — Quarles & Brady, LLP

(57) ABSTRACT

Cancer patients make antibodies to tumor-derived proteins that are potential biomarkers for early detection. Twenty-eight antigens have been identified as potential biomarkers for the early detection of basal-like breast cancer (Tables 1, 2). Also, a 13-AAb classifier has been developed that differentiate patients with BLBC from healthy controls with 33% sensitivity at 98% specificity (Table 3).

7 Claims, 1 Drawing Sheet

(56) References Cited

U.S. PATENT DOCUMENTS

| | | | |
|---|---|---|---|
| 2019/0004051 | A1 | 1/2019 | Labaer |
| 2019/0062728 | A1 | 2/2019 | Labaer |
| 2019/0162725 | A1 | 5/2019 | Magee |
| 2019/0302122 | A1 | 10/2019 | Katchman |
| 2020/0182887 | A1 | 6/2020 | LaBaer |
| 2020/0308573 | A1 | 10/2020 | LaBaer |
| 2020/0386754 | A1 | 12/2020 | LaBaer et al. |
| 2020/0400671 | A1 | 12/2020 | LaBaer et al. |
| 2020/0407792 | A1 | 12/2020 | LaBaer et al. |
| 2021/0163926 | A1 | 6/2021 | LaBaer et al. |

FOREIGN PATENT DOCUMENTS

| | | | |
|---|---|---|---|
| WO | 2013063126 | A2 | 5/2013 |
| WO | 2013090364 | A1 | 6/2013 |
| WO | 2014077725 | A1 | 5/2014 |
| WO | 2014120902 | A1 | 8/2014 |
| WO | 2014143954 | A2 | 9/2014 |
| WO | 2014145458 | A1 | 9/2014 |
| WO | 2015148202 | A1 | 10/2015 |
| WO | 2015167678 | A1 | 11/2015 |
| WO | 2015167678 | A8 | 11/2015 |
| WO | 2016141044 | A1 | 9/2016 |
| WO | 2017048709 | A1 | 3/2017 |
| WO | 2017075141 | A1 | 5/2017 |
| WO | 2017075141 | A8 | 5/2017 |
| WO | 2017123648 | A1 | 7/2017 |
| WO | 2017218677 | A2 | 12/2017 |
| WO | 2018013531 | A1 | 1/2018 |
| WO | 2018013531 | A8 | 1/2018 |
| WO | 2019136169 | A1 | 7/2019 |
| WO | 2019241361 | A1 | 12/2019 |

OTHER PUBLICATIONS

Blanchard, A. A., et al. "Claudins 1, 3, and 4 protein expression in ER negative breast cancer correlates with markers of the basal phenotype." Virchows Archiv 454.6 (2009): 647-656.
Blows, F. M., et al. "Subtyping of breast cancer by immunohistochemistry to investigate a relationship between subtype and short and long term survival: a collaborative analysis of data for 10,159 cases from 12 studies." Plos Medicine vol. 7 Issue 5 e1000279 (2010).
Carvalho, Leda Viegas de, et al. "Molecular characterization of breast cancer in young Brazilian women." Revista da Associação Médica Brasileira 56.3 (2010): 278-287.
Chapman, C., et al. "Autoantibodies in breast cancer: their use as an aid to early diagnosis." Annals of oncology 18.5 (2007): 868-873.
Desmet, C., et al. "Multiplexed immunoassay for the rapid detection of anti-tumor-associated antigens antibodies." Analyst 136.14 (2011): 2918-2924.
European Patent Office, Extended European Search Report for application 15868296.3. Mailed on Jul. 23, 2018.
Guler, G., et al. "Fragile histidine triad protein, WW domain-containing oxidoreductase protein Wwox, and activator protein 2? expression levels correlate with basal phenotype in breast cancer." Cancer: Interdisciplinary International Journal of the American Cancer Society 115.4 (2009): 899-908.
Ihemelandu, C. U., et al. "Molecular breast cancer subtypes in premenopausal African-American women, tumor biologic factors and clinical outcome." Annals of surgical oncology 14.10 (2007): 2994-3003.
International Searching Authority, International Search Report and Written Opinion for application PCT/US2015/064792. Mailed on Mar. 21, 2016.
Invitrogen: ProtoArray Human Protein Microarray:, Sep. 16, 2013, Retrived from the internetL URL:https://www.thermofisher.com/content/dam/LifeTech/global/technical-reference-library/s2s/dbourdon/protoarray_v5_general_brochure_long.pdf.
Kelly, C. M., et al. "Agreement in risk prediction between the 21-gene recurrence score assay (Oncotype DX®) and the PAM50 breast cancer intrinsic classifier™ in early-stage estrogen receptor-positive breast cancer." The oncologist 17.4 (2012): 492.
Kuroda, H., et al. "Basal cytokeratin expression in relation to biological factors in breast cancer." Human pathology 39.12 (2008): 1744-1750.
Lin, C.-H., et al. "Molecular subtypes of breast cancer emerging in young women in Taiwan: evidence for more than just westernization as a reason for the disease in Asia." Cancer Epidemiology and Prevention Biomarkers 18.6 (2009): 1807-1814.
Nagele, E., et al. "Diagnosis of Alzheimer's disease based on disease-specific autoantibody profiles in human sera." PloS one 6.8 (2011): e23112.
Ramachandran, N., et al. "Tracking humoral responses using self assembling protein microarrays." Proteomics—Clinical Applications 2.10-11 (2008): 1518-1527.
Voduc, D., et al. "The combination of high cyclin E and Skp2 expression in breast cancer is associated with a poor prognosis and the basal phenotype." Human pathology 39.10 (2008): 1431-1437.
Wang, J. et al. Abstract 874: Autoantibody biomarker discovery in basal-like breast cancer using nucleic acid programmable protein array. Breast Cancer Research and Treatment, vol. 74(19), Oct. 1, 2014.
Zaenker, P. et al. "Serologic autoantibodies as diagnostic cancer biomarkers—a review." Cancer Epidemiology and Prevention Biomarkers 22.12 (2013): 2161-2181.
Mange et al (Clin Cancer Res, 2012, 18(7): 1992-2000).
Neuman et al (Annals of Surgical Oncology, 2011, 15(7): 2034-2041).
Richardson et al (British Journal of Cancer, 1999, 80(12): 2025-2033).
Wang, et aL, "Plasma Autoantibodies Associated With Basal-like Breast Cancers," Cancer Epidemiology, Biomarkers & Prevention, Published Online First, Jun. 12, 2015, pp. 1158-1055.
Badve, et aL, "Basal-like and Triple-negative Breast Cancers: a Critical Review with an Emphasis on the Implications or Pathologists and Oncologists," Modern Pathology, vol. 24, pp. 157-167 (2011).

* cited by examiner

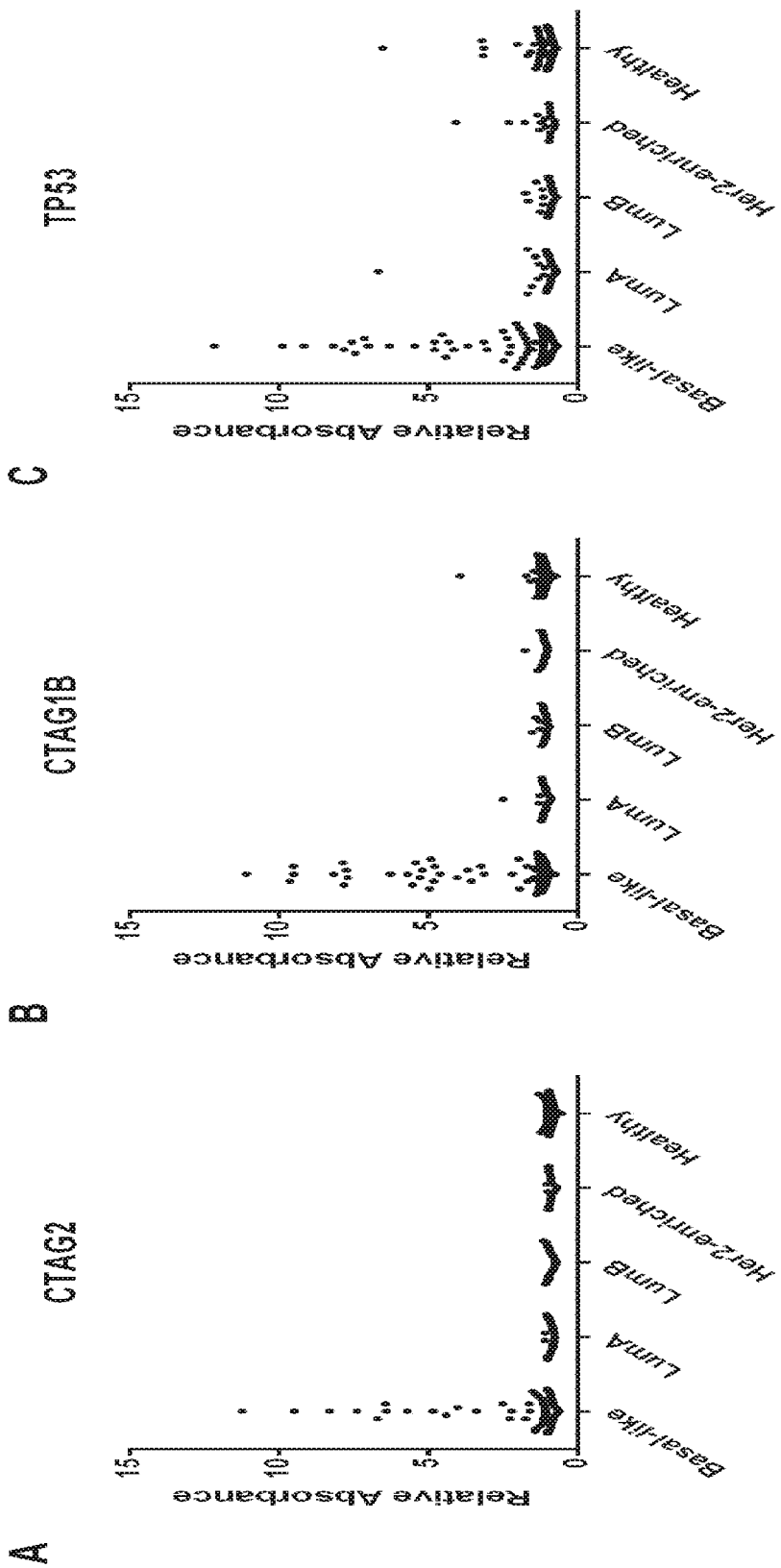

PLASMA AUTOANTIBODY BIOMARKERS FOR BASAL LIKE BREAST CANCER

CROSS-REFERENCE TO RELATED APPLICATIONS

This application is a continuation of U.S. patent application Ser. No. 16/743,906, filed Jan. 15, 2020, which claims priority to International Patent Application No. PCT/US2015/064792, filed Dec. 9, 2015, which claims priority to U.S. Provisional Patent Application No. 62/089,631 filed on Dec. 9, 2014, the disclosures of which are incorporated by reference herein in their entireties.

STATEMENT OF GOVERNMENT RIGHTS

This invention was made with government support under U01 CA117374 awarded by the National Institutes of Health. The government has certain rights in the invention.

TECHNICAL FIELD

The disclosure herein related to biomarkers for cancer and more particularly to autoantibody biomarkers for breast cancer.

BACKGROUND

Despite significant improvement in early detection by routine mammography, breast cancer remains a global challenge. Current screening mammography only detects 70% of breast cancers. Breast tumors associated with high breast density and highly proliferative cancers are frequently not detected by screening. Therefore, there is an urgent need for biomarkers that can detect potentially invasive breast cancer in their early stages.

Like other cancers, breast cancer is heterogeneous, comprising multiple molecular subtypes with unique characteristics of prognosis, response to treatment and risk of recurrence. This heterogeneity affects the biomarker discovery, requiring both larger sample sizes and different statistical approaches from traditional methods of evaluation. A biomarker (or panel) may perform well for one molecular subtype but not another.

Current screening mammography also has limitations in detecting the basal-like subtype cancers. The fraction of BLBC within all breast cancer cases detected by mammography is less than its natural frequency in the general population, indicating that BLBC was under-diagnosed by routine mammography and more frequently detected as interval breast cancer. Early detection of BLBC by screening mammography is compromised partly by its high proliferation rate and lack of suspicious features of regular breast malignancy, such as microcalcifications, irregular spiculated masses or pleomorphic microcalcifications. Moreover, BLBC is often present in women less than 50 years old, who are not recommended for routine mammogram by US Preventative Service Task Force mammogram guidelines.

Considering the high frequency of disease in women younger than 50 years old, a potentially large population with BLBC does not benefit from present breast cancer screening and would benefit from a molecular test for the disease. Therefore, there is an urgent need for biomarkers that can detect potentially invasive basal like breast cancer in their early stages.

SUMMARY

We have identified 28 antigens as potential biomarkers for the early detection of basal like breast cancer. These biomarkers were selected out of 10,000 tumor antigens in a sequential screening study and yielded supporting evidence in a blinded validation study. These biomarkers should be useful components of diagnostic tests and personalized therapeutics for breast cancer.

All references cited throughout are hereby incorporated by reference herein.

BRIEF DESCRIPTION OF DRAWINGS

FIG. 1 depicts dotplots of AAb responses in various breast cancer subtypes.

DETAILED DESCRIPTION

Notably, the sensitivity of a subtype-specific biomarker can never be higher than the prevalence of that subtype in the population where it is tested. The ability to find biomarkers for cancer detection with high sensitivities has likely been impaired by this effect. This is especially true for disease subtypes that are less common in the overall population. Basal like breast cancer is a breast cancer subtype with aggressive disease progression and poor prognosis. It overlaps significantly with triple negative breast cancer (TNBC), a clinical pathological subtype characterized by negative tissue staining of estrogen receptor (ER), progesterone receptor (PR), and the absence of human epidermal growth factor receptor 2 (HER2) amplification.

TNBC is associated with African American ethnicity, younger age, advanced stage at diagnosis and poorer outcomes. However, TNBC itself has been found to be molecularly heterogeneous in two recent studies. Among patients with TNBC, a core basal subtype with expression of epidermal growth factor receptor (EGFR) or basal cytokeratin 5/6 (CK5/6) characterized a group of patients with worse prognosis than the rest of the patients with TNBC. This five marker subtyping (ER-, PR-, HER2-, and either EGFR+or CK5/6+) is highly correlated with BLBC defined by gene expression profiling.

Current screening mammography has limitations in detecting the basal-like subtype. The fraction of BLBC within all breast cancer cases detected by mammography is less than its natural frequency in the general population, indicating that BLBC was under-diagnosed by routine mammography and more frequently detected as interval breast cancer. Early detection of BLBC by screening mammography is compromised partly by its high proliferation rate and lack of suspicious features of regular breast malignancy, such as microcalcifications, irregular spiculated masses or pleomorphic microcalcifications.

Moreover, BLBC is often present in women less than 50 years old, who are not recommended for routine mammogram by US Preventative Service Task Force mammogram guidelines. Considering the high frequency of disease in women younger than 50 years old, a potentially large population with BLBC does not benefit from present breast cancer screening and would benefit from a molecular test for the disease.

In practical terms, molecular diagnostic tests for the early detection of cancer should be performed on readily accessible samples, like plasma, because they are likely to be performed on many individuals. The concentration of many cancer biomarkers in blood tends to be very low because it relies upon secretion by cancer cells which are few in number in the pre-clinical stage. Moreover, the biomarker gets diluted in a large volume of plasma volume and only a fraction of the secreted biomarker gets distributed to the plasma.

An alternative strategy is to exploit the ability of the immune system to detect the presence of tumor cells through the generation of autoantibodies. These responses of the adaptive immune system against target tumor antigens amplify the signals from the minute amount of tumor proteins released from cancer tissue.

We have previously conducted an autoantibody biomarker discovery for breast cancer on our nucleic acid programmable protein array (NAPPA) platform. NAPPA allows us to display thousands of freshly produced full length human proteins on glass slides without the need of protein purification and has been applied to the study of disease specific antibodies in diseases ranging from infectious to autoimmune to cancers. In that study, we took a three stage study design to identify autoantibody markers from 4988 human proteins.

The goal for the discovery stage 1 was to eliminate non-reactive and uninformative (i.e. no difference between case and control) antigens and reduce the total number of antigens. The top 761 antigens were selected based on differential reactivity between cases and controls. The goal for the training stage II was to identify candidate autoantibody markers. The goal for the blinded validation stage III was to validate potential biomarkers. This yielded a panel of 28 markers showing sensitivities in the 10-30% range with specificities from 80-100%.

However, the sample cohort used in this study was a mixed population of predominantly women with ER+PR+ breast cancer. Therefore, the utility of these markers in subtypes like BLBC or Her2+ are likely limited, considering their relatively low percentage among breast cancer patients. Here, we aimed to identify BLBC specific autoantibodies by profiling humeral immune responses of BLBC patients against 10,000 human proteins.

One challenge associated with the use of "omics" technology to study a homogeneous cancer subtype is the requirement of a large number of samples to have sufficient power of analysis. To this end, our study was supported by the Polish Breast Cancer Study, in which over 2386 breast cancer patients were enrolled.

Paraffin embedded tissue samples were collected for immunohistochemical (IHC) analysis and disease classification. We successfully collected plasma samples from 145 patients classified to be basal-like subtype by either PAM50 gene signature based on mRNA expression profiling, or tissue IHC staining of ER, PR, HER2, EGFR and CK5/6. In addition, for each patient, we also collect plasma sample from an age, gender and location matched healthy donor. Here, we first profiled sero-reactivity against ~10,000 human proteins in 45 BLBC patients and 45 matched controls.

Candidate antigens were selected, assayed for their autoantibodies in BLBC using customized NAPPA and enzyme-linked immunosorbant assay (ELISA), and validated using an independent patient cohort in a blind fashion. See, for example, "Tracking humoral responses using self assembling protein microarrays," Proteomics Clin Appl. 2008 Oct 2(10-11):1518-27. A biomarker signature was also developed to discriminate basal-like tumors from age and location matched healthy individuals. We further evaluated the specificity of the panel of autoantibodies to basal-like tumors using a set of patients with other breast cancer subtypes.

The 28 antigens that we have identified as potential biomarkers for the early detection of basal like breast cancer are (Table 1, Table2): P53 (TP53), NY-ESO-1 (CTAG1B), NY-ESO-2 (CTAG2), RNF216, PPHLN1, PIP4K2C, ZBTB16, TAS2R8, WBP2NL, DOK2, PSRC1, MN1, TRIM21, POU4F1, SSMEM1, LMO4, BCL2, KRT8, TSGA13, PVRL4, SNRK, DYRK3, RNF32, JUNB, KCNIP3, CCDC68, CSN3, TRAIP, which are available at the DNASU Plasmid Repository at the Bio Design Institute of the Arizona State University, Tempe, Ariz. In addition, we also developed a classifier to differentiate patients with BLBC from healthy controls with 33% sensitivity at 98% specificity (Table3).

We designated samples as positive if they exceeded antigen-specific cutoffs for at least 2 of the 13 antigens. Antigen-specific cutoffs were set to achieve 98% classifier specificity by adjusting the specificity at the antigen level to 98.7%.

A point of novelty is the identification of the 28 antigens that are potential biomarkers for early detection of basal like breast cancer (Table 1, 2). Many of these 28 antigens have not been previously associated with basal like breast cancer. In addition, we also developed a classifier to differentiate patients with BLBC from healthy controls with 33% sensitivity at 98% specificity (Table3).

TABLE 1

Training and Validation Statistics for Potential basal-like breast cancer Biomarkers

| Antigen | Training (Cohort1&2: basal, n = 95; healthy, n = 95) | | | Validation (Cohort3: basal, n = 50; healthy, n = 50) | |
|---|---|---|---|---|---|
| | sensitivity | specificity | cutoffs | sensitivity | specificity |
| CTAG1B | 0.213 | 0.979 | 1.606 | 0.200 | 1.000 |
| CTAG2 | 0.191 | 0.979 | 1.149 | 0.180 | 0.960 |
| TRIM21 | 0.158 | 0.979 | 1.208 | 0.140 | 0.860 |
| RNF216 | 0.110 | 0.978 | 1.369 | 0.043 | 0.956 |
| MN1 | 0.105 | 0.979 | 1.311 | 0.060 | 0.920 |
| PIP4K2C | 0.105 | 0.979 | 1.200 | 0.020 | 1.000 |
| TP53 | 0.084 | 0.979 | 3.171 | 0.200 | 1.000 |
| ZBTB16 | 0.084 | 0.979 | 1.393 | 0.040 | 0.980 |
| TRAIP | 0.074 | 0.979 | 2.682 | 0.040 | 0.980 |
| DOK2 | 0.074 | 0.979 | 1.164 | 0.060 | 1.000 |
| CSN3 | 0.063 | 0.979 | 1.955 | 0.060 | 0.980 |
| PPHLN1 | 0.063 | 0.979 | 3.394 | 0.080 | 1.000 |
| TAS2R8 | 0.063 | 0.979 | 1.064 | 0.080 | 0.940 |
| SSMEM1 | 0.063 | 0.979 | 1.562 | 0.060 | 0.960 |
| DYRK3 | 0.063 | 0.979 | 1.462 | 0.040 | 0.940 |
| KRT8 | 0.053 | 0.979 | 1.645 | 0.060 | 0.960 |
| LMO4 | 0.053 | 0.979 | 1.199 | 0.020 | 0.980 |
| WBP2NL | 0.053 | 0.979 | 1.991 | 0.060 | 0.980 |
| JUNB | 0.042 | 0.979 | 1.165 | 0.020 | 0.960 |
| TSGA13 | 0.042 | 0.979 | 1.313 | 0.020 | 0.980 |
| PVRL4 | 0.042 | 0.979 | 0.899 | 0.020 | 0.920 |
| CCDC68 | 0.042 | 0.979 | 2.438 | 0.000 | 0.940 |
| BCL2 | 0.042 | 0.979 | 1.160 | 0.000 | 1.000 |
| SNRK | 0.032 | 0.979 | 4.127 | 0.020 | 0.960 |
| PSRC1 | 0.032 | 0.979 | 1.372 | 0.120 | 0.960 |
| KCNIP3 | 0.032 | 0.979 | 0.973 | 0.000 | 0.960 |
| POU4F1 | 0.032 | 0.979 | 0.992 | 0.080 | 0.940 |
| RNF32 | 0.021 | 0.979 | 1.445 | 0.040 | 0.980 |

TABLE 2

Performance of 28 antigens in all subtypes of breast cancer.

| | Sensitivity | | | | |
|---|---|---|---|---|---|
| Antigen | basal-like | luminal A | luminal B | Her2-enriched | Specificity |
| CTAG1B | 0.208 | 0.033 | 0.045 | 0.056 | 0.979 |
| CTAG2 | 0.188 | 0.000 | 0.000 | 0.000 | 0.979 |
| TP53 | 0.124 | 0.033 | 0.000 | 0.056 | 0.979 |
| RNF216 | 0.088 | 0.133 | 0.095 | 0.000 | 0.978 |
| PPHLN1 | 0.083 | 0.100 | 0.182 | 0.000 | 0.979 |
| PIP4K2C | 0.076 | 0.100 | 0.091 | 0.111 | 0.979 |
| ZBTB16 | 0.069 | 0.000 | 0.000 | 0.000 | 0.979 |
| TAS2R8 | 0.069 | 0.000 | 0.000 | 0.056 | 0.979 |
| WBP2NL | 0.069 | 0.100 | 0.091 | 0.000 | 0.979 |
| DOK2 | 0.069 | 0.133 | 0.091 | 0.056 | 0.979 |
| PSRC1 | 0.063 | 0.033 | 0.045 | 0.056 | 0.979 |
| MN1 | 0.062 | 0.100 | 0.000 | 0.056 | 0.979 |
| TRAIP | 0.062 | 0.067 | 0.045 | 0.000 | 0.979 |
| CSN3 | 0.062 | 0.100 | 0.182 | 0.000 | 0.979 |
| TRIM21 | 0.055 | 0.033 | 0.000 | 0.056 | 0.979 |
| POU4F1 | 0.048 | 0.033 | 0.000 | 0.222 | 0.979 |
| SSMEM1 | 0.048 | 0.033 | 0.136 | 0.000 | 0.979 |
| LMO4 | 0.041 | 0.033 | 0.000 | 0.056 | 0.979 |
| BCL2 | 0.041 | 0.033 | 0.045 | 0.000 | 0.979 |
| KRT8 | 0.034 | 0.033 | 0.000 | 0.056 | 0.979 |
| TSGA13 | 0.034 | 0.000 | 0.000 | 0.056 | 0.979 |
| PVRL4 | 0.034 | 0.000 | 0.000 | 0.000 | 0.979 |
| SNRK | 0.028 | 0.000 | 0.045 | 0.000 | 0.979 |
| DYRK3 | 0.028 | 0.033 | 0.045 | 0.000 | 0.979 |
| RNF32 | 0.028 | 0.033 | 0.000 | 0.056 | 0.979 |
| JUNB | 0.021 | 0.000 | 0.000 | 0.000 | 0.979 |
| KCNIP3 | 0.014 | 0.033 | 0.000 | 0.000 | 0.979 |
| CCDC68 | 0.007 | 0.000 | 0.000 | 0.000 | 0.979 |

TABLE 3

Cutoffs for 13-AAb classifier

| Antigen | Cutoff |
|---|---|
| CTAG1B | 1.606 |
| CTAG2 | 1.176 |
| TP53 | 3.171 |
| RNF216 | 1.459 |
| PPHLN1 | 3.448 |
| PIP4K2C | 1.201 |
| ZBTB16 | 1.925 |
| TAS2R8 | 1.178 |
| WBP2NL | 2.120 |
| DOK2 | 1.164 |
| PSRC1 | 1.461 |
| MN1 | 1.687 |
| TRIM21 | 5.509 |

An example of how a patient sample would be handled to detect and diagnose basal-like breast cancer using one or more of the discovered biomarkers in a kit with a suitable detection agent is as follows.

A patient's plasma sample is obtained, and then subsequently tested for autoantibody responses against the proposed protein panels. Briefly, protein targets are produced either freshly in situ or purified ahead of time, and immobilized on solid surface. A plasma sample is then incubated with these protein targets. Labeled secondary antibody that can recognize human immunoglobulins are used for the signal read out. Accordingly, data such as that shown in FIG. 1 can be obtained and used to detect and/or diagnose basal-like breast cancer.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. A method comprising:
   contacting a serum or plasma sample obtained from a human subject to a panel of tumor antigens, wherein said human subject is a female patient less than 50 years old; and
   detecting binding of at least two tumor antigens with antibodies in the serum or plasma, wherein the antigens are detectably labeled and the at least two tumor antigens are RNF216, PPHLN1, PSRC1, and TRIM21.

2. The method of claim 1, wherein said detecting comprises utilizing an enzyme-linked immunosorbent assay (ELISA).

3. The method of claim 1, wherein said detecting occurs at a specificity of at least 97.9%.

4. The method of claim 1, wherein the detectable label is a labeled secondary antibody.

5. A method comprising:
   (i) obtaining a serum or plasma sample from a human;
   (ii) contacting the serum or plasma sample to a panel of detectably labeled tumor antigens comprising PSRC1, TRIM21, RNF216, PPHLN1; and
   (iii) analyzing proteins in the contacted sample for the presence of autoantibodies specific for at least two tumor antigens of the panel, wherein analyzing comprises an enzyme-linked immunosorbent assay (ELISA).

6. The method of claim 5, wherein the panel further comprises one or more detectably labeled tumor antigens selected from PIP4K2C, ZBTB16, TAS2R8, WBP2NL, DOK2, MN1, POU4F1, SSMEM1, LMO4, BCL2, KRT8, TSGA13, PVRL4, SNRK, DYRK3, RNF32, JUNB, KCNIP3, CCDC68, CSN3, TRAIP, P53 (TP53), NY-ESO1 (CTAG1B), and NY-ESO2 (CTAG2).

7. The method of claim 5, wherein the detectable label is a labeled secondary antibody.

* * * * *